United States Patent [19]

Sorensen et al.

[11] 4,258,705

[45] Mar. 31, 1981

[54] MAGNETIC SYSTEM FOR USE IN SEALING BODY OPENINGS

[75] Inventors: Erik L. Sorensen, Helsinge; Per Wolff, Birkerød; Hans-Ole Larsen, Farum, all of Denmark

[73] Assignee: Coloplast A/S, Espergaerde, Denmark

[21] Appl. No.: 942,857

[22] Filed: Sep. 15, 1978

[51] Int. Cl.³ .............................................. A61B 19/00
[52] U.S. Cl. .................................... 128/1 R; 128/283; 3/1
[58] Field of Search ................. 128/1 R, 1.3, 1.4, 283, 128/DIG. 25; 3/1

[56] References Cited

U.S. PATENT DOCUMENTS

| | | | |
|---|---|---|---|
| 2,243,529 | 5/1941 | Grossman et al. | 128/DIG. 25 X |
| 3,565,073 | 2/1971 | Giesy | 128/283 |
| 3,939,821 | 2/1976 | Roth | 128/1 R |
| 3,952,726 | 4/1976 | Hennig et al. | 128/1 R |
| 4,154,226 | 5/1979 | Hennig et al. | 128/1 R |

FOREIGN PATENT DOCUMENTS

| | | | |
|---|---|---|---|
| 2363563 | 6/1975 | Fed. Rep. of Germany | 128/283 |
| 2537573 | 2/1977 | Fed. Rep. of Germany | 128/DIG. 25 |
| 2648222 | 4/1978 | Fed. Rep. of Germany | 128/283 |

Primary Examiner—Robert W. Michell
Assistant Examiner—T. J. Wallen
Attorney, Agent, or Firm—Lawrence Rosen

[57] ABSTRACT

A magnet system for sealing devices for artificial or natural intestinal or similar ducts, comprising a ring-magnet to implant in the tissue around the duct and a rod-shaped center magnet member mounted in a more or less soft sealing member to be in sealing contact with the walls of the duct. The improvement is that the center magnet member comprises at least two, in practice usually two or three, axial aligned individual magnets acting together so as to resist axial displacement; the individual poles are positioned to resist tilting of the center magnet member relative the axis of the duct and the ring-shaped magnet member.

3 Claims, 17 Drawing Figures

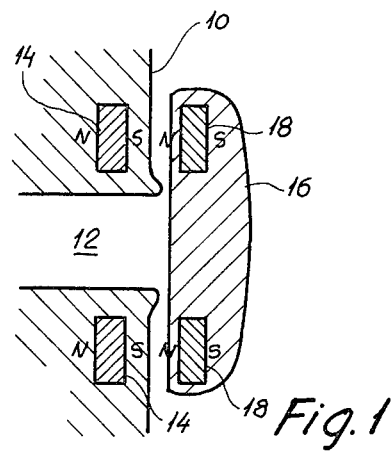 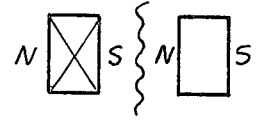
Fig. 1    Fig. 1a
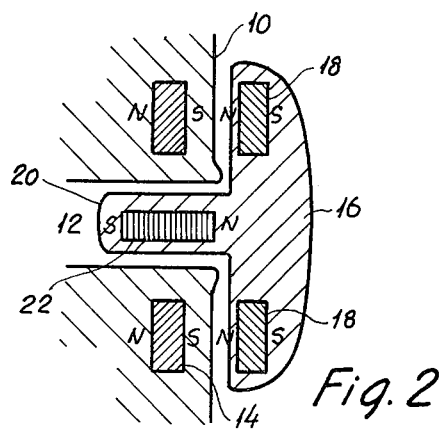 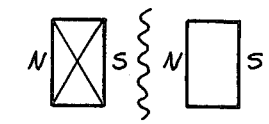
Fig. 2    Fig. 2a
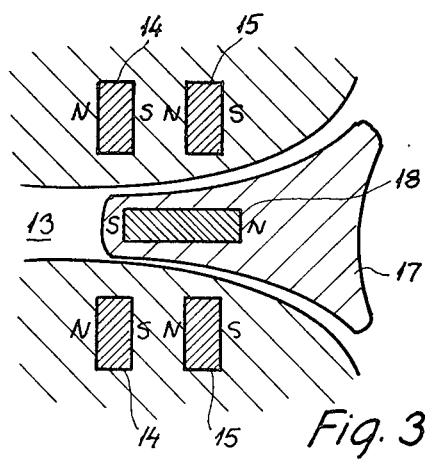 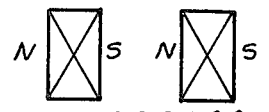
Fig. 3    Fig. 3a

MAGNETIC SYSTEM FOR USE IN SEALING BODY OPENINGS

FIELD OF THE INVENTION

The present invention relates to a magnet system for sealing devices for artificial and natural intestinal and artificial urethra outlet ducts, comprising a ring-shaped magnet adapted to be implanted in the tissue surrounding the intestinal duct near its outlet opening and with its axis substantially coaxial with the axis of the duct, and a rod-shaped center magnet member mounted axially in a sealing member comprising a sealing material adapted to come into sealing contact with the inner wall of the intestinal duct near its opening, the rod-shaped magnet member in "use" position being inside and substantially coaxial with the ring-shaped magnet.

BACKGROUND OF THE INVENTION

Many colostomy and ileostomy patients have an artificial intestinal opening in the abdominal wall, and the flow of solid, liquid, semi-liquid and gaseous waste products therethrough cannot be controlled at will. A similar problem exists when an artificial urethra opening has been made in the abdominal wall and in cases of anal incontinence. One way of solving the problems involved herein is to affix some form of bag or pouch to the abdomen or seat of the patient so as to collect the waste material and remove and replace the bag at suitable intervals. Another way is to close the opening by some form of plug or cover plate and remove and reinsert or replace it at intervals in order to drain the intestine or urethra. The pouch or bag as well as the plug or cover may be kept in place by various kinds of means, such as straps, adhesives or combinations thereof. Comparatively recently there has also been developed magnetic systems for maintaining such devices in place.

Recently there has been developed sealing systems comprising a more or less cylindrical and more or less soft expansible or compressible sealing body adapted to be inserted into outer parts of the intestinal duct or artificial urethra in sealing contact with its walls. Centrally in the sealing body there is a magnet and in the tissue surrounding the outer part of the duct in question there is a ring-magnet which keeps the sealing member in place. Such sealing systems are disclosed in U.S. patent application Ser. No. 801,326 (now U.S. Pat. No. 4,154,226) or British Pat. application No. 15731/77.

The present invention is an improvement of magnetic systems for use in sealing natural and artificial intestinal and urethra openings of the general type mentioned, especially for use in connection with sealing bodies not connected with collecting pouches or bags. However, in some cases it may be expedient to connect the magnetic system with some form of collecting bags. The invention is not concerned with sealing pads, sealing tampons, collecting pouches or similar devices as such, nor with means for allowing the escape of gases without causing too much embarrassment and such means will therefore only be mentioned or described in so far as necessary for understanding the magnetic system.

BRIEF DESCRIPTIONS OF THE DRAWINGS

FIGS. 1, 2, 3, and 4 schematically show various prior art magnetic systems of the general kind here concerned, whereas FIGS. 5, 6, 7, and 8 schematically show various embodiments of the magnetic closing system according to the present invention.

DISCUSSION OF PRIOR ART

So far as we are aware, the first proposal for using magnets in closing intestinal openings is represented by U.S. Pat. No. 3,565,073 to Giesy. It is here proposed to implant, by surgery, a ring-shaped magnet around the artificial intestine and to affix an "appendage" (which may comprise a collecting pouch) to the abdominal wall by magnetic forces, the appendage containing a magnet or magnetic material to cooperate with the ring-shaped magnet. A magnetic system typically involved herein is schematically illustrated by FIG. 1. Here, 10 is the abdominal wall, 12 the intestinal duct, 14 a ring-shaped magnet implanted in the soft tissue around intestinal duct, 16 some cover device (pouch, lid, cover plate etc.; for clarity shown in some distance from the abdominal wall but in practice closely adjacent it) and 18 one or more magnets provided in closure device 16. As will be seen, the magnetic forces act between magnets 14 and 18 (one of which may in fact not be a magnet but merely a magnetic material), perpendicularly to the abdominal wall and perpendicularly to the sealing surface as still more schematically illustrated in FIG. 1a, showing only the magnets, the sealing surface being denoted by a wave line.

The disadvantages of this system is that the sealing pressure is inversely proportional to some high power of the distance between the two magnets; to maintain the cover in place the pressure must be high which will cause discomfort to the patient and in the long run necrosis of the tissue. If by mistake the cover device is removed from its proper place, the magnetic forces will rapidly be too weak to pull it back to the correct position.

The best magnetic system for purposes as those here concerned so far developed is represented by U.S. Pat. No. 3,952,726 to Hennig. It comprises an axially magnetized ring-shaped permanent magnet positioned around the intestinal opening and a magnetic sealing cap means for closing the intestinal opening. The sealing cap member comprises a cap adapted to contact the abdominal wall of the patient and at least one ferromagnetic material attracted by the implanted ring-magnet, as well as an axially magnetized permanent magnetic core member positioned (when the cap member is in closing position) inside the implanted ring-shaped magnet. The core member is axially magnetized in a manner so as to increase the attraction between the implanted magnet and the magnets in the closing member when spaced a wide distance away (say, 10–20 mm according to the patent), and reduces the magnetic attraction at a close distance (say, 3–7 mm). Thus, the magnetic forces are comparatively constant over a distance. This system is illustrated in FIG. 2, which shows the cover means a little distance away from its proper sealing position, which is in contact with the abdominal wall. The ring-shaped magnet implanted around the body opening 12 attracts as in FIG. 1 the magnet, magnets or magnetic material 18 positioned in the cap member 16, the latter also provided with a cylindrical plug 20 projecting from the proper cover into the stoma (intestinal opening) and containing a core magnet 22. The magnets and sealing surface are illustrated in FIG. 2a. The magnetic forces are perpendicular to the abdominal wall and the sealing surface parallel with that wall and hence perpendicular to the magnetic forces. In a modification of the system, the magnets are omitted in the cap part. The magnetic system of U.S. Pat. No. 3,952,726 has proved useful with many patients but has some disadvantages. The distance with constant magnetic force is rather small so that the usable range is small and accordingly individual adjustments have to be made for each patient and a very high quality of surgery is essential. Difficulties have been encountered with adipose patients and if a patient looses or gains weight (i.e. experiences alterations in the thickness of subcutaneous fat) the tightness of the sealing may get lost.

German Patent Application No. P 2625234.6 (Hennig) discloses a magnetic system especially for closing the anus in cases of anal incontinence but may conceivably be modified for use for closing other body openings. In this system two ring-shaped magnets are implanted around the outer part of the intestine (rectum). The closing is made by a more or less conical stopper with a sealing surface being more or less parellel to the rectum and surrounding parts of the seat. An axial magnet means is provided in the stopper to cooperate with the two implanted ring-magnets in such a way as to give at least an approximately constant axial force in a certain range of distance between the implanted magnets and the magnet means of the stopper. The system is illustrated in FIG. 3. Here two ring-shaped magnets 14 and 15 are implanted in the body around rectum 13 which is to be sealed by stopper 17 containing an axially aligned magnet (or magnetic material) 18, poles here like in FIGS. 1 and 2 being identified with the letters N and S, representing north and south, respectively. The magnets and sealing surface alone are schematically shown in FIG. 3a. In this system the sealing surface is poorly defined and it will be difficult to present leakage. If adapted to artificial intestinal openings (stomas) there may be a risk for the stopper of penetrating too deep into the intestine; and even if it does not, sealing will be poor. In any case, closing means of this type must be made individually and are not subject to mass production.

U.S. patent application No. 801,326 and its British counterpart No. 15731/77, mentioned above, disclose devices for closing intestinal openings, comprising an axially magnetized ringshaped magnet implanted around the outer parts of the body opening (artificial or natural intestine) and cooperating with a rod-shaped magnet (or magnetic material) to insert into the body opening. The sealing is provided by some soft material surrounding the inserted rod-shaped magnet, either a soft, radially compressible elastic material such as a foam plastic or some similar material; or by a radially expansible material, e.g. a cellulosic material more or less similar to that used for female monthly hygiene. The sealing surface is parallel to the magnetic axis and the sealing pressure results from elastic compression or swelling of the sealing material and is not dependent on the magnetic forces as in the devices mentioned above. Instead of one implanted ring-shaped magnet there may be two. The system is shown schematically in FIG. 4, the magnets and sealing surface along in FIG. 4a in case of one implanted ring magnet, in FIG. 4b in case of two implanted ring magnets. The system is applicable to artificial intestinal or urethra openings (as illustrated) as well as to rectum, e.g. in case of anal incontinence. The artificial intestinal duct 12 with openings in abdominal wall 10 is surrounded by a ring-shaped magnet 14 with axial poles oriented as shown. The intestine is closed by a plug-like sealing member 21 made of an elastic compressible material or by an expansible material (e.g. expansible under the influence of water or other liquid). Member 21 contains an axially magnetized rod-shaped magnet (or magnetic material) oriented as shown. This system has the advantage that the axial magnetic force is zero when the sealing plug is in the correct sealing position but large if the plug is moved away from that position. The function of the sealing is independent of the distance from the implanted magnetic ring or rings to the skin of the patient; in other words the function is not too dependent on quality of surgery or on weight loss or gain of the patient and also the system will tend to prevent intestinal waste material to come into contact with skin and only permit it to come into contact with mucous membranes. On the other hand the system has the disadvantage that it must be guided in the sidewise or radial direction and will have an inherent strong tendency to tilt, i.e. have its axis form an angle with the axis of the ring magnet. In "dead center" inside the ring magnet, the system is in equilibrium. But even small movements away from center may lead to instability in the form of unsymmetrical forces away from center, inversely proportional to some third or even higher power of the distance. The sidewise guidance is provided by the compressible or expandible material of the plug but even if they may give some protection to the tissues surrounding the artificial (or natural) intestine, the tendency to tilt may lead to undesirable high pressure on part of the tissues and this again may lead to necrosis and/or displacement of the implanted magnet. The tilting tendency may also lead to leakage of the sealing, which may be very embarrassing. It can be mentioned that by experiment it has been shown that tilting tendency in an actual embodiment of this system was such that after having been tilted 1/10 radian from the coaxial position relative the axis of the ring magnet and with the turning point (tilting center) being in the middle of the axis of the ring magnet, the center magnet had a tendency to augment the degree of tilting, the force to do that being 0.07 Newton.cm per 1/10 radian.

A further disadvantage of this system is some tendency to axial instability of the center magnet. This may lead either to the expulsion of the plug from the intestine or to its penetration deeper into the intestine. Especially the latter tendency may be dangerous because the sealing may thereby harm the deeper part of the intestinal system or block it so as to result in severe obstipation. Actually there have been cases where patients have needed hospital assistance to remove sealing devices from a position deep in the intestinal duct.

OBJECTS OF THE INVENTION

It is the object of the present invention to provide a magnetic system for the purpose stated which is free of the drawbacks discussed hereinbefore, notably the drawbacks of the system discussed with reference to FIGS. 4 and 4a. It is emphasized again that the invention is only concerned with the magnetic system and that the sealing proper may be carried out in any convenient manner, including resilient, elastic, compressible or expansible materials and members as those disclosed in the abovementioned U.S. and UK patent specifications. Also, the system may be provided with venting openings or such venting openings may be closed or protected by some suitable filtering material including active carbon and other odour-removing materials.

Thus it is a main object of the invention to provide a magnetic system of the kind concerned which is stable in the axial direction as well as stable against tilting, whereby the system will not provoke damage or necrosis to the tissues even when possessing sufficient magnetic force to ensure good sealing of the sealing member against the wall of the duct.

A further object is to provide a system of the kind concerned which will exert greater resistance against being pushed from the normal "use" position into the duct than from the "use" position out from the duct.

DETAILED DESCRIPTION OF THE INVENTION AND ITS SEVERAL EMBODIMENTS

These objects are achieved in a magnet system for artificial and natural intestinal and artificial urethra ducts, comprising an implanted ring-shaped magnet substantially coaxial with the duct and a rod-shaped center magnet member mounted axially in sealing member comprising a sealing material to come into sealing contact with the intestinal duct near its opening, the rod-shaped center magnet member in "use" position being inside and substantially coaxial with the ring-shaped magnet, if according to the invention the rod-shaped magnet member comprises at least two axially aligned individual magnets acting together in "use" position so as to resist any axial displacement, the individual magnets of the rod-shaped center magnet member being positioned so as to resist tilting of the axis of the rod-shaped center magnet member relative the axis of the ring-shaped magnet.

This means that the overall effect of the magnets in the center magnet member is a neutral axial force when it is in "use" position coaxial with the ring magnet, the latter surrounding part of the center magnet member. Though in the axial sense the system acts as if it had only two poles, i.e. as if it were only one magnet, in the radial sense the individual poles will be effective and counteract tilting, which is a substantial improvement over the prior art system illustrated hereinbefore by FIGS. 4 and 4a. The present system is stable against tilting; this stability is defined as the momentum of power by which the rod-shaped center magnet member will try to re-assume its starting position coaxial with the ring-magnet when tilted 1/10 radian on the middle of the axis of the ring-magnet and the said momentum is >0 when the system is stable against tilting.

The magnets may be of any convenient ferromagnetic material. However, it may be particularly advantageous to use magnets of PtCo, $SmCo_5$ or other alloys of rare earth metals and cobalt though these systems cannot be used where identical poles are very close to each other.

Figure 4:
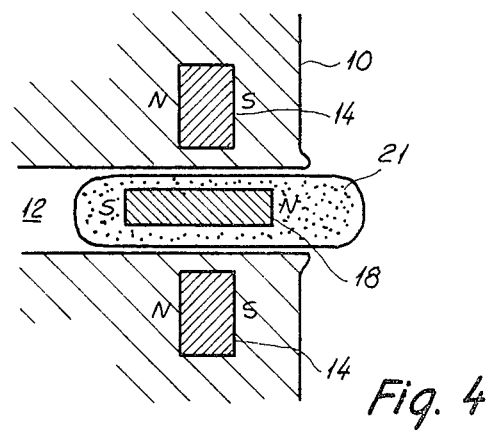
Figure 4A:
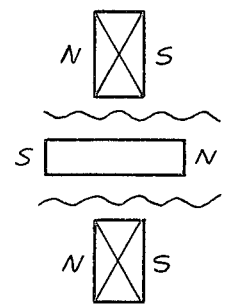
Figure 4B:
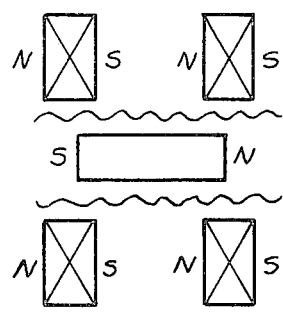

The ring magnet may be of one of the types known and used, for instance, in the systems described with reference to FIGS. 2, 3, or 4.

The center magnet member must contain at least two magnets but the arrangement thereof may vary. Physically, the magnets of the center magnet member are embedded or enclosed in some suitable material such as a plastic material or a rubber material inert to the mucous membranes, body fluids, and to the material constituting the sealing material proper. A suitable material can readily be found by those skilled in the art. Likewise, the implanted ring magnet will be embedded in a material, preferably some plastic material recognised in the art and discussed in some of the prior art references discussed hereinbefore. Also, the ring-shaped implanted magnet may be subdivided into encapsulated sectors of rings.

As the sealing member with the rod-shaped center magnet is inserted into the intestinal duct, the axial magnetic forces acting on it pass through a repulsion maximum so that a certain mechanic force must be exerted in order to insert the seal. As the plug gets nearer the plane of the ring magnet, the forces change to attraction forces pulling the sealing member or rather the center magnet member into an axial equilibrium position inside the ring magnet, the center magnet member behaving as if it consisted of only one magnet. When the overall field of magnetic forces is symmetrical about the middle plane of the ring magnet—which it may be in certain embodiments of the invention and which it is in the prior art system illustrated in FIG. 4—a further movement of the plug into the intestine will at first be counteracted by the magnetic field but a certain distance away from the symmetry plane repulsive magnet forces will take over and push the sealing member further into the intestinal duct. Such penetration is highly undesirable and may be dangerous for the patient, and in an advantageous embodiment of the invention therefore the magnets of the rod-shaped center magnet member are arranged unsymmetrically relative to the middle plane of the ring-shaped magnet in "use" position, the orientation being such that the force required to push the center magnet member from "use" position further into the duct is larger than that required to pull it from "use" position out from the duct. Preferably the force required to push the center magnet member further into the duct from "use" position is at least about twice that required to pull it the opposite direction.

Some embodiments of the magnet system according to the invention are illustrated in FIGS. 5-8 of the drawing. In all instances, like in FIGS. 1-4, the center magnet member is shown in "use" position and the ring magnet is oriented with the north pole (N) facing inwards the body of the patient and the south (S) pole facing the epidermis of the patient. In actual practice this is the most common orientation but it may well be the opposite. If the position of the poles of the ring magnet is reversed relative that shown in the drawing, the orientation of the individual magnets of the rod-shaped center magnet member must of course also be reversed.

As a rule, a total axial force of the magnet system of 3.5 Newton will suffice because of the friction in the duct.

Figure 5:
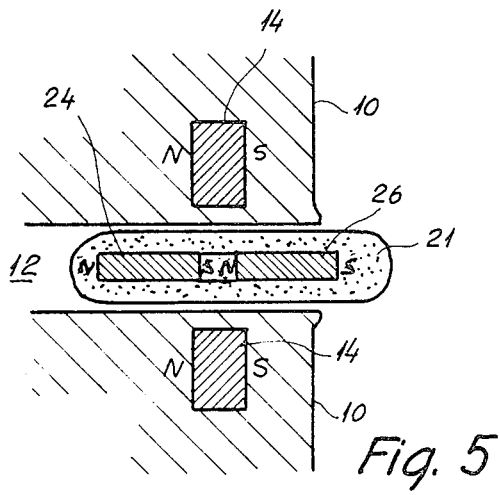
Figure 5A:
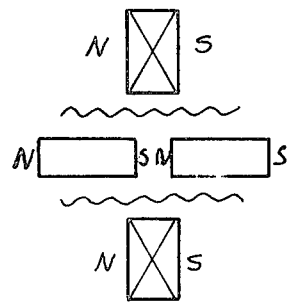

One embodiment of the magnet system according to the invention is illustrated in FIG. 5, the magnets and sealing surface shown schematically in FIG. 5a in analogy with the prior art systems discussed. In FIG. 5, stoma 12 opens in abdominal wall 10 and is surrounded by ring-shaped magnet 14 axially magnetized as shown with poles N and S. The stoma is closed by a plug 21 surrounded by the two cylindrical and axially aligned magnets (encapsulated in some common cover material) 24 and 26. Seen as a hole, these two magnets may function as one in the same manner as that shown in FIG. 4; but if a tilting occurs two "auxiliary" poles, formed by the ends of the two magnets 24, 26 facing each other, will be repulsed by the ring magnet, the "auxiliary" N pole being near the plane of the N pole of the ring magnet, and the "auxiliary" S pole being near the S pole of the ring magnet.

This system has the advantage of being very stable in axial direction. Force which keeps the system in equilibrium position is larger than with a single center magnet. By experiments with identical magnets it has been found that the maximum force to get the plug into position in a system like that of FIG. 4 and 4a was 500 g, and likewise the maximum force to lead the plug further into the intestine was 500 g. However, in a system according to FIG. 5 and 5a the maximum force in both cases was 800 g.

The system according to FIG. 5 also has the advantage of very little tendency to tilt, and of very low radial forces in use position; this again means that the pressure on the soft surrounding tissues is small and hence the risk of necrosis small.

Accordingly, in this embodiment the center magnet member comprises two magnets arranged in some distance from one another and both with the poles oriented as the poles of the ring-shaped implanted magnet. The distance between the magnets is not very critical and may, for instance, be of the order of about the thickness of the ring magnet. The space between the two magnets of the center magnet member may be filled with air or with some magnetically inert material.

Figure 6:
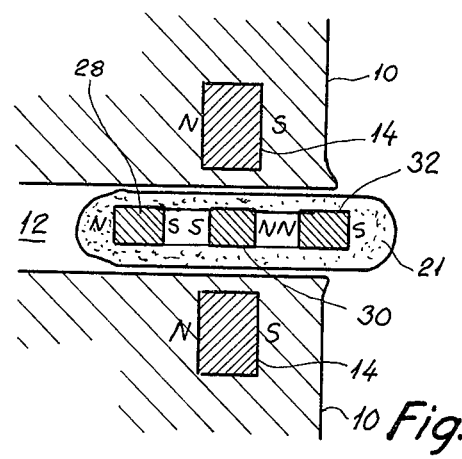
Figure 6A:
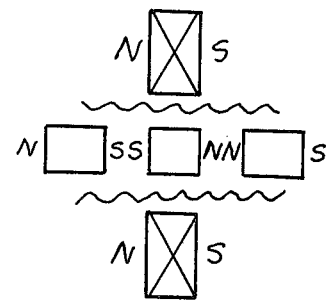

Another embodiment of the system according to the invention is illustrated in FIGS. 6 and 6a. Again, stoma 12 opens in abdominal wall 10 and is surrounded by ring-magnet 14 oriented as shown by the letters N S. Plug 21 surrounds three aligned and suitably embedded cylindrical magnets 28,30,32 arranged as shown; the middle one is adapted to be just in plane with the ring-shaped magnets in closing position and with its poles oriented oppositely those of the ring-magnet. At both ends of the middle cylindrical magnet there are cylindrical magnets oppositely oriented, i.e. with S pole facing S pole and N pole facing N pole. This system has largely the advantages of that of FIG. 5 and additionally there is a reduced tendency of the plug to penetrate deeper into the intestine than the normal closing netrate deeper into the intestine than the normal closing position. The tendency to tilt is very low. In an experiment similar to that mentioned above, the maximum force to get the plug into position was 500 g and the maximum force to get the plug further into intestine 1600 g.

Figure 7:
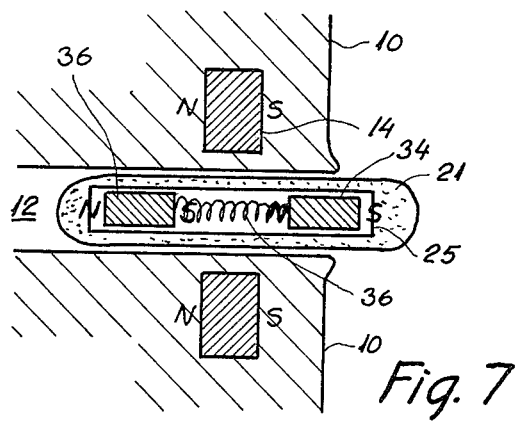
Figure 7A:
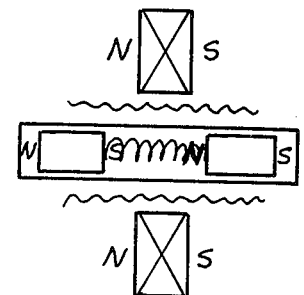

In a third embodiment, illustrated in FIGS. 7 and 7a, a stoma 12 debouches in abdominal wall 10 and is surrounded by ring-shaped magnet 14, oriented as shown. A plug 21 is adapted to close the stoma and that plug surrounds a capsule 25 containing two cylindrical, axially aligned magnets 34 and 36. Between them there is a spring 36 compressed by magnetic forces during insertion of plug 21 with its contents into the correct position; however, once the first magnet (36 in FIG. 7) has passed the central plane as represented by the ring-shaped magnet, it is pushed further by the spring, giving an effect in the closure system resembling that of a snap-lock. Other advantages of this system are similar to those discussed with reference to FIG. 5.

Figure 8:
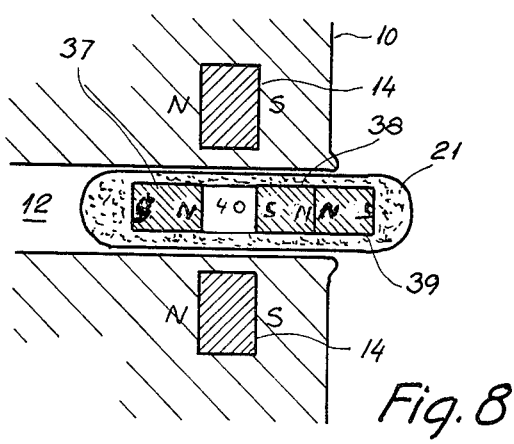
Figure 8A:
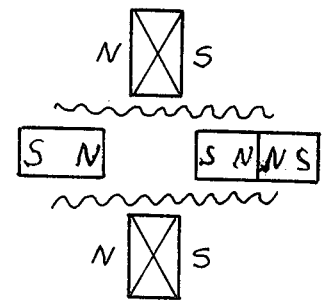

A further embodiment is illustrated in FIG. 8. Again, a stoma debouches in abdominal wall 10 and is surrounded by a ring magnet 14 oriented as shown. A plug or seal 21 is adapted to close the stoma and the seal 21 contains a rod-shaped center magnet member encapsulated by a suitable plastic material (not shown except by a line). The center magnet member comprises three individual magnets two of which are arranged with a space 40, filled with air or some other magnetically inert material between them, whereas the third is in direct contact with the outermost of the two firstmentioned magnets. The orientation of magnets is as shown on FIGS. 8 and 8a i.e. with the poles of the magnets 37,38 adjacent the space oriented in the opposite sense of those of the ring-magnet and supplemented with a further magnet 39 adjacent the outermost 38 of the other magnets and oriented opposite that, i.e. as the ring-magnet 14. "Outermost" in this context means nearest to the outer end of the duct.

This embodiment has the advantages of that of FIG. 5 plus the added advantage of resisting very strongly any tendency to push sealing member further into the intestinal duct, past the ring magnet, i.e. resisting strongly any movement from "use" position to the left as shown in the drawing.

In this embodiment the radial stability, i.e. stability against tilting, is very high and the safety force is much higher than the closing force, usually about the double thereof or more. In this connection, the closing force is defined as the force required to pull the center magnet member from "use" position out of the stoma (to the right in the drawing) and the safety force the force required to push the center magnet member from "use" position further into the duct (to the left in the drawing).

In a practical form of the embodiment of FIG. 8, made of $SmCO_5$ and having the following dimensions:
ring magnet 14:
  outer diameter 48 mm
  inner diameter 34 mm
  axial width 7 mm
center magnet member:
  all magnets cylindrical, diameter 10 mm
  magnet 37, axial length 9 mm
  space 40 between magnets, 4 mm
  magnet 38, axial length 11 mm
  magnet 39, axial length 20 mm
the closing force was 3.3 Newton, the safety force 6.6 Newton and the stability against tilting (as defined hereinbefore) 0.17 Newton.cm:1/10 radian.

The high safety force may be further increased by placing a further magnet—oriented as magnet 39—at the innermost end of the center magnet member in axial contact with magnet 37.

What is claimed is:

1. A sealing device for artificial and natural intestinal and artificial urethra ducts comprising (a) a ring-shaped, axially magnetized magnet member with north pole and south pole and adapted to be implanted in the tissue surrounding the duct near its outlet opening and with its axis substantially coaxial with the axis of the duct, and (b) a sealing member moveable between an inactive position outside the duct and a use position inside the duct near its outlet opening, substantially coaxial with the duct and with part of the sealing member within the implanted ring-shaped magnet member, said sealing member comprising a rod-shaped center magnet member and a sealing material surrounding the center magnet member and adapted to be in sealing contact in use position with the inner wall of the duct, wherein the rod-shaped center magnet member comprises at least two longitudinally aligned individual magnets arranged at a distance from each other and separated by a magnetically inert space, the poles of both magnets being oriented in use position in the same north-south direction as the poles of the ring-shaped implanted magnet member, the magnetically inert space between the two magnets of the center magnet member in use position being positioned within the implanted ring-shaped magnet member and substantially perpendicular to the plane of the implanted ring-shaped magnet member and substantially central with respect thereto, the poles of the individual magnets of the center magnet member being oriented in the use position relative the orientation of the poles of the implanted ring-shaped magnet member so that magnetic forces exerted by the magnets resisting attempts to push the center magnet member from use position farther into the duct are larger than those resisting attempts to pull it from use position out of the duct, said longitudinally aligned magnets acting together in use position so as to resist any axial displacement, the individual magnets of the rod-shaped magnet member being positioned in use position so as to resist tilting of the axis of the rod-shaped center magnet member relative the axis of the implanted ring-shaped magnet member.

2. The sealing device of claim 1 wherein the center magnet member comprises three longitudinally aligned individual magnets arranged at a distance from each other and separated by magnetically inert spaces, the middle magnet in use position oriented with its poles opposite the orientation of the poles of the implanted ring-shaped magnet member, which has an axially middle part, and situated in use position with an axially part flush with the axially middle part of the implanted ring-shaped magnet member, the poles of the two other magnets of the center magnet member being oriented in the same north-south direction as the poles of the implanted ring-shaped magnet member.

3. The sealing device of claim 1 wherein the center magnet member comprises three longitudinally aligned individual magnets, a magnetically inert space being arranged between the two magnets which in use position are farthest away from the outlet opening of the duct and in use position situated within the implanted ring-shaped magnet member, the two magnets of the center magnet member adjacent the magnetically inert space having their poles oriented oppositely the north-south orientation of the poles of the implanted ring-shaped magnet member, the third magnet being positioned in axial contact with one of the two magnets which is adjacent to the magnetically inert space of the two other magnets, and which in use position are farthest from the outlet opening of the duct and have their poles oriented in the same north-south direction as the north-south poles of the implanted ring-shaped magnet member.

* * * * *